United States Patent [19]

Jaeschke et al.

[11] 4,219,145
[45] Aug. 26, 1980

[54] CARTON WITH ADJUSTABLE AIR PASSAGES

[75] Inventors: Harold R. Jaeschke, Milwaukee; Thomas R. Patmore, Elm Grove, both of Wis.; George Webinger, Minneapolis, Minn.

[73] Assignee: Champion International Corporation, Stamford, Conn.

[21] Appl. No.: 25,012

[22] Filed: Mar. 29, 1979

[51] Int. Cl.² .......................... A61L 9/04; B65D 5/36
[52] U.S. Cl. ........................................ 229/8; 239/60; 229/4.5; 239/59
[58] Field of Search .................. 229/9, 10, 11, 4.5, 229/19, 20; 239/58, 59, 60, 49

[56] References Cited

U.S. PATENT DOCUMENTS

| | | | |
|---|---|---|---|
| 2,247,600 | 7/1941 | Brennan et al. | 239/59 X |
| 2,738,225 | 3/1956 | Meek | 239/60 X |
| 4,125,189 | 11/1978 | Fujimoto et al. | 229/9 |
| 4,163,518 | 8/1979 | Webinger | 229/8 |

FOREIGN PATENT DOCUMENTS

| | | | |
|---|---|---|---|
| 121737 | 10/1930 | Austria | 229/11 |
| 281201 | 1/1931 | Italy | 239/59 |

*Primary Examiner*—Davis T. Moorhead
*Attorney, Agent, or Firm*—Evelyn M. Sommer

[57] ABSTRACT

Disclosed are a carton having adjustable air passages and a blank for forming it. The carton is formed of slidable inner and outer tapered sleeves having complementary spaced openings. The openings are positioned to provide open air passages when the inner sleeve is slid to a first position, and to close the passages as the inner sleeve is moved toward a second position. This carton is especially adapted to hold an air freshening medium during storage and to permit controlled exposure of it to the air during use.

7 Claims, 8 Drawing Figures

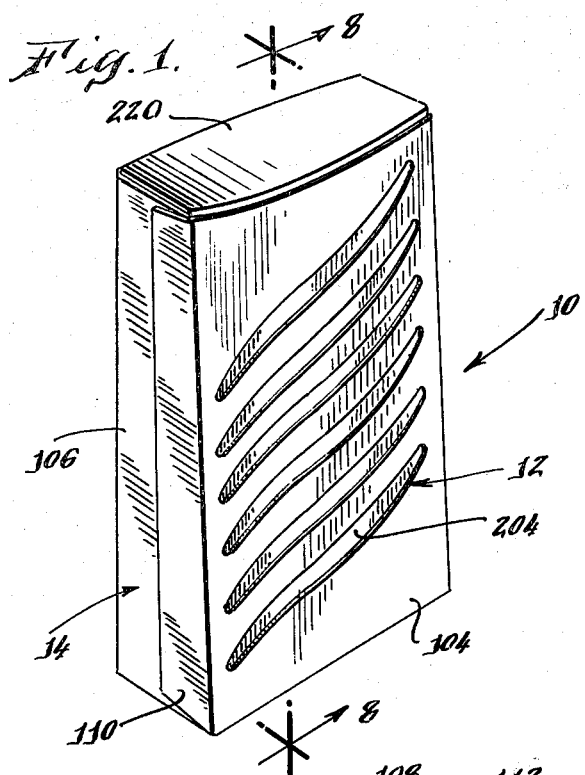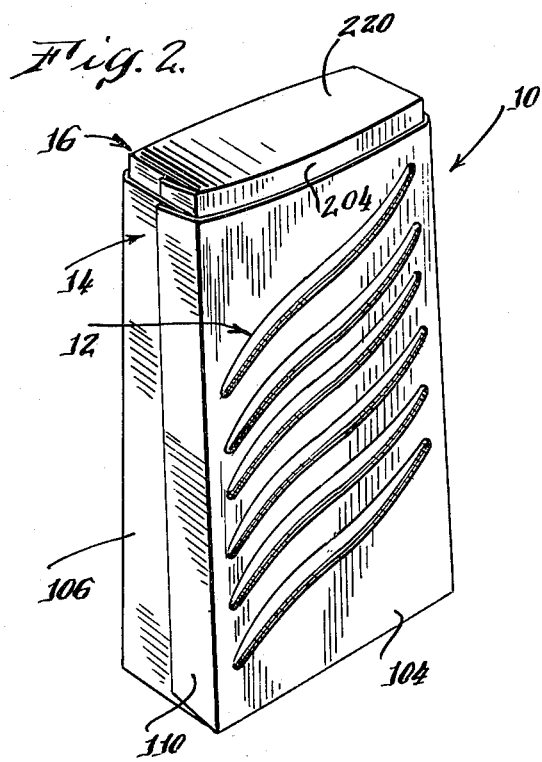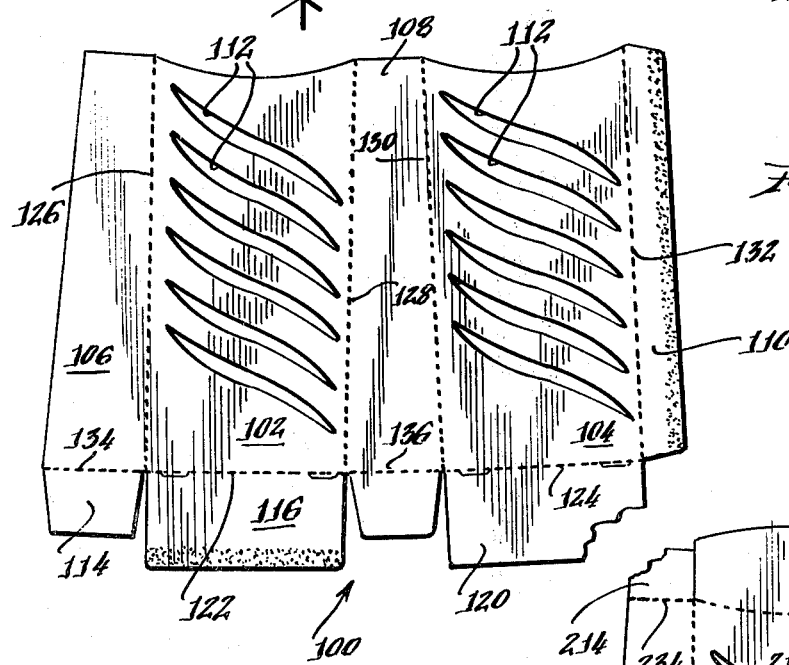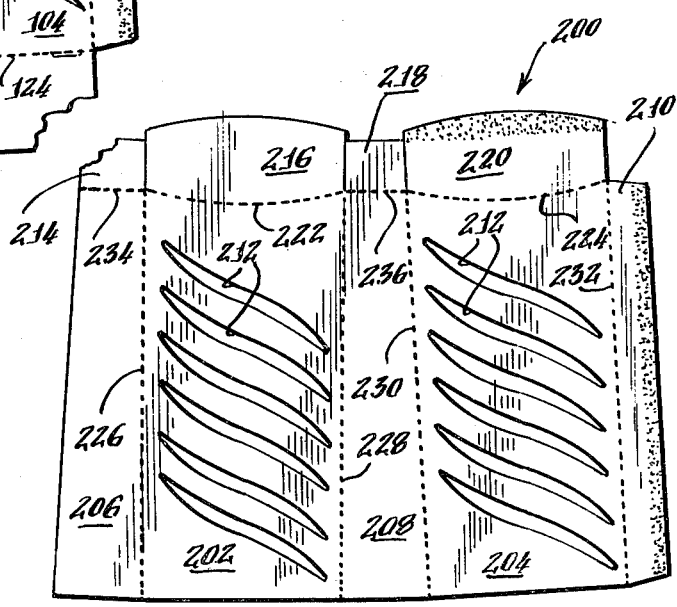

U.S. Patent Aug. 26, 1980 Sheet 2 of 2 4,219,145
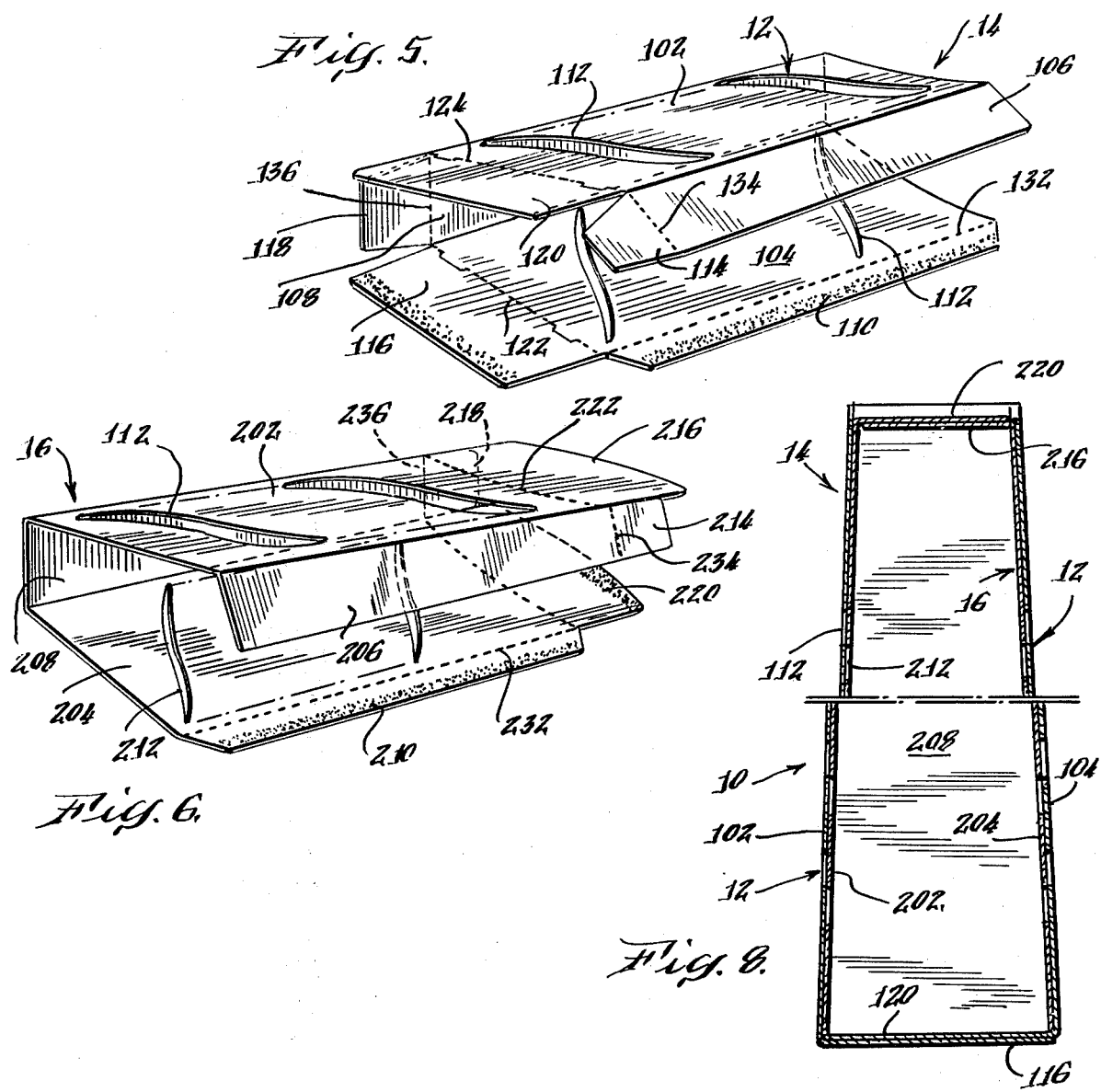
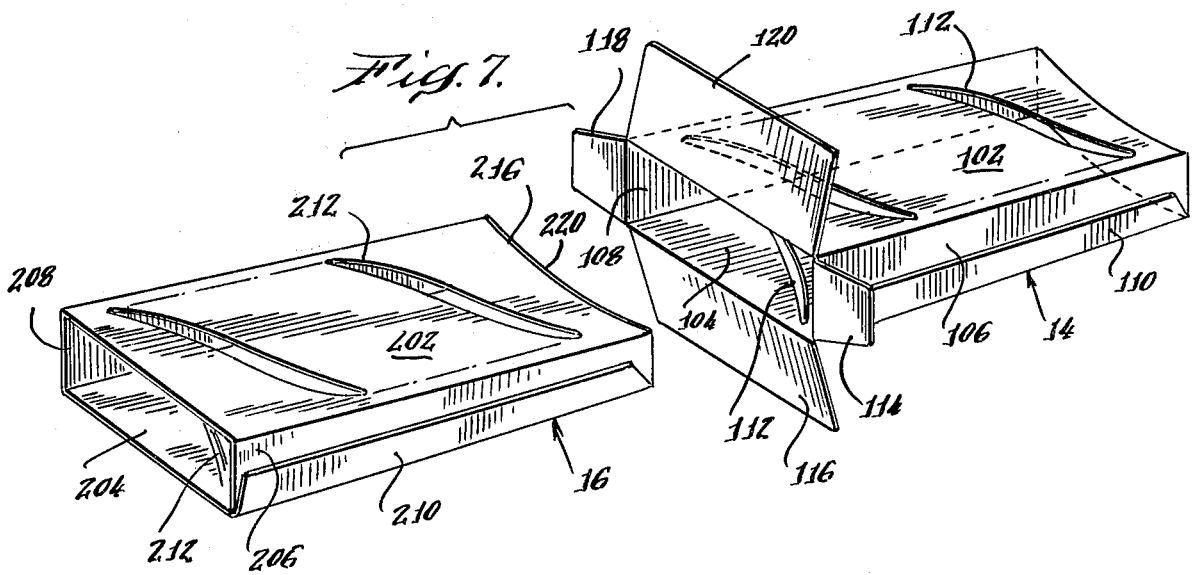

CARTON WITH ADJUSTABLE AIR PASSAGES

BACKGROUND OF THE INVENTION

The present invention relates to cartons, and more particularly to a carton for holding an active material and controllably releasing it to the air.

There are a variety of active materials for use in household and commercial applications which it is desirable to contact with and release into the ambient air. Among these are insecticides and air fresheners which can be packaged in solid form in containers having air passages which permit release. Frequently, products of this type are packaged in containers having a plurality of openings which are closed at the time of purchase but which are opened at the time of use to allow room air to circulate over the surface of a solid active material.

In one type of carton, the openings are covered with a panel of release paper. When the consumer is ready to use the product, such as an air freshener, the release paper is peeled from the face of the container to allow room air to begin circulating through the openings. In another type of carton, the consumer activates the air freshener material by squeezing to release an encapsulated active ingredient. In yet another type of carton, holes in an outer carton wall are opened or closed by a slidable inner sheet which acts as a valve.

Molded plastic containers, usually consisting of a molded shell and a separate molded cover, have been employed to hold air freshener material. However, while molded plastic containers have an aesthetically pleasing appearance, the cost of making them is higher than might be desired. The shell and cover must be molded in separate operations and stored in unassembled form until the air freshener insert is loaded. The cover then must be glued or otherwise secured to the shell to provide a closed container. The extra time required for the separate manufacturing and assembly operations results in added manufacturing costs for the package and ultimately for the product sold therein. The fact that the molded shells and covers must be shipped and stored in their molded form will also cause increased transportation and storage costs.

SUMMARY OF THE INVENTION

It is an object of the present invention to provide an improved carton having a plurality of adjustable air passages therein.

It is another object of the present invention to provide an improved carton for storing an active material prior to actual use and to easily open to permit controlled release of the active material to ambient air during use.

It is yet another object of the present invention to provide an improved package for controllably releasing active materials to the air which has inner and outer slidable members constructed of a sheet material wherein the inner and outer members can be slidably moved between open and closed positions.

These and other objects are accomplished according to the present invention which provides an improved carton and a blank for its construction. The carton has a plurality of adjustable air passages and comprises: (a) a first tapered sleeve forming an outer carton unit, said first sleeve being closed at at least one end and having a plurality of spaced openings therein; and (b) a second tapered sleeve forming an inner carton unit, said second sleeve being nested within said first sleeve and being slidable between a first position and a second position, said second sleeve being closed at at least the end opposite said end closed in said first sleeve and having a plurality of spaced openings therein arranged complementarily to said spaced openings in said outer carton unit to align with the openings therein when said inner carton unit is in said first position, and to align with the spaces between said openings in said outer carton unit when said inner carton unit is in said second position.

BRIEF DESCRIPTION OF THE DRAWINGS

The invention will be better understood and its advantages will be more apparent from the following detailed description, especially when read in light of the attached drawings wherein:

FIG. 1 is a perspective view of one embodiment of a carton according to the present invention showing the air passages in the closed position;

FIG. 2 shows the carton shown in FIG. 1 with the openings in their operative, open position;

FIGS. 3 and 4 show the blanks for forming the inner and outer carton units for forming a carton as shown in FIG. 1, the blanks being viewed in plan, from what will be their inside surfaces, ready for folding;

FIGS. 5 and 6 show the initial stages of folding of the blanks shown in FIGS. 3 and 4;

FIG. 7 shows the final stages of construction of the composite carton shown in FIG. 1; and FIG. 8 is a cross-sectional view taken along line 8—8 in FIG. 1.

DETAILED DESCRIPTION OF THE INVENTION

The present invention provides a two component carton having adjustable air passages and a blank for forming it. The carton is especially adapted for use in storing a solid active material such as an insecticide or a room air freshener during transportation and display, and then functioning as a dispenser for the active material by controllably releasing the active material to ambient air through adjustable air passages during use. The carton is formed of slidable inner and outer tapered sleeves having complementary, spaced openings. The openings are positioned to permit room air to circulate into contact with the active material and back to the room in their open position but to also permit their partial or complete closure as the sleeves are moved to a second closed position.

The carton shown as 10 in FIG. 1 is a presently preferred embodiment according to this invention. It is shown to stand erect about its vertical axis. The carton 10 shown in the drawing has a substantially rectangular cross-section at any point perpendicular to the vertical axis. While this embodiment is preferred, it is to be understood that the carton can have other cross-sectional shapes perpendicular to the axis along which it slides. For example, it is possible to have virtually any cross-section such as triangular, square, pentagonal, hexagonal, octagonal, and the like. The objects of the present invention are equally well attained despite the particular cross-section, and can be attained even with circular and oval cross-sections. It is to be further understood that while there are definite advantages in having the carton stand such that it is adjustable about its vertical axis, it is equally possible to have the inner and outer members slide along the horizontal axis.

With this general explanation, the following detail will be directed toward a preferred embodiment of the invention which is particularly well suited for use in dispensing air fresheners which are held in solid form within the carton.

Referring now to FIGS. 1 and 2, carton 10 is shown in FIG. 1 in the closed position and is shown in FIG. 2 in the fully open position. It will be understood that the openings 12 can be adjusted to any degree between the first position wherein they are completely open and the second position wherein they are completely closed. Adjustment between the open and the closed positions is obtained by moving outer carton unit 14 relative to inner carton unit 16 to obtain the desired degree of alignment and therefore opening of the apertures in the inner carton 16 and outer carton unit 14. The openings 12 are shown in the front and back panels, but this is preferred only. The openings can be positioned as desired.

The detail of the construction of the preferred embodiment will be better understood by viewing FIGS. 3 through 7 which show the various stages of construction of the carton. FIG. 3 shows an outer blank 100 for forming the outer carton unit 14 and FIG. 4 shows an inner blank 200 for forming the inner carton unit 16.

FIG. 3 shows outer blank 100 for forming the outer carton unit 14. This blank 100 is being viewed from what will be its inside surface. As will be seen in FIG. 5, the blank 100 can rest on back panel 104 for assembly by folding the other panels upwardly from the horizontal to the final form. The blank comprises rectangular front panel 102, rectangular rear panel 104, and trapezoidal side wall panels 106 and 108. These parts are of essentially the same dimensions as those of the like parts of the inner carton blank 200. If desired, to obtain a better sliding engagement, the outer and inner carton units 14 and 16 can differ in overall dimension by about 1 to 2 times the thickness of the sheet material for forming the cartons. The sheet materials used in forming the carton can be any of those typically employed for making disposable cartons. Preferably, a paperboard material or a laminate of a paperboard with a plastic material will be employed.

Referring again to FIG. 3, the outer carton blank 100 also shows a glue flap 110 as well as flaps 114, 116, 118 and 120 for closing one end of the outer carton unit 14. Apertures or openings 112 are provided in spaced relation on both the front and the back panels. The openings are arranged such that in the final construction they will be complementary to similar spaced openings 212 in the inner carton unit 16 to align with the openings 212 therein when said inner carton unit 16 is in the first or open position (as shown in FIG. 2), and to align with the spaces between the openings 112 in the outer carton unit 14 when the inner carton unit 16 is in the second or closed position (as shown in FIG. 1).

It is preferred that the openings 112 be of essentially the same shape and size as the openings 212 in the inner carton blank 200. Because it is desired in the preferred embodiment of the invention to enable the complete closing of the openings, the space between the openings 112 on the outer carton blank 100, as measured along any line parallel to the vertical axis of the final carton 10, must be of greater vertical extent than the openings 112 themselves. The openings 212 in the inner carton blank 200 must be similarly positioned and spaced so that alignment with openings 112 in the constructed carton 10 will be facilitated.

In assembling the outer carton unit 14 from the blank 100, panels 102, 104, 106, 108 and glue flap 110 are folded about fold lines 126, 128, 130 and 132 as shown in FIG. 5. The blank 100 is then glued in folded position by securing glue flap 110 to side panel 108.

The inner blank 200 is shown in FIG. 4 to comprise a rectangular front panel 202, a rectangular back panel 204 and two trapezoidal side panels 206 and 208. As in FIG. 3, the blank 200 in FIG. 4 is being viewed from what will be its inside surface. As will be seen in FIG. 6, the blank 200 can rest on back panel 204 with the other carton panels being folded up from the horizontal to the final form. A glue tab 210 is provided for sealing the inner blank 200 into a sleeve having a substantially rectangular cross-section after folding as shown in FIG. 6. Both the front panel 202 and the rear panel 204 have spaced openings 212 therein.

The inner carton unit 16 is preferably closed at at least one end, and this will preferably be the top end where according to the drawing flaps 214, 216, 218 and 220 are provided for folding over and forming the closed end. Flap 216 is bendable from front panel 202 about a curved fold line 222. Similarly, flap 220 can be bent from rear panel 204 about curved fold line 224.

Referring to FIG. 6, the sequence of construction of the inner carton unit 16 can be seen more clearly where the panels 202, 206, 204, 208 and glue flap 210 are folded about intermittent score lines 226, 228, 230 and 232. Then, glue flap 210 is adhered to end wall 206. Tabs 214 and 218 are folded about fold lines 234 and 236 and then overlayed by upper tabs 216 and 220 which are folded about curved fold lines 222 and 224, respectively. Tabs 216 and 220 are preferably adhesively secured in known manner.

Referring now to FIG. 7, there is shown the next stage in construction of the carton wherein the inner carton unit 16 in fully constructed form is being slidably passed into partially assembled outer carton unit 14. After insertion of inner carton unit 116 into outer carton unit 216, flaps 114, 116, 118 and 120 are folded about fold lines 122, 124, 134 and 136 to close the bottom end of the outer carton unit 14 and form the final carton as shown in FIG. 1.

Preferably the outer carton unit 14 will have the opposed front and rear panels 102 and 104, cut away at the top end thereof to permit grasping of the inner carton unit 16 to slide it between the open and closed positions.

Referring again to FIG. 4 wherein the blank 200 for forming the inner carton unit 16 is shown in detail, it will be noted that the curved fold lines 222 and 224 will cause the extreme upper portion of the inner carton unit 16 to be slightly bowed. Thus, while the cross-section at this upper edge will remain substantially rectangular, it will have a degree of bow which will provide for a better frictional engagement between the inner carton unit 16 and the outer carton unit 14. This arrangement improves the inherent frictional engagement between the two slidable members, and makes it possible to achieve better positioning of the two carton members to obtain any desired degree of opening which will better resist dislocation.

The carton has good stability because the cross-section at the base, when stood vertically along its long axis, is smaller than the cross-section at the top, thereby providing a low center of gravity and good resistance to being knocked over.

The above description has been for the purpose of teaching those skilled in the art how to make and use the present invention and is not meant to detail all those obvious modifications and variations thereof which will be apparent upon reading. It is intended, however, to include these obvious modifications and variations within the scope of the invention which is defined by the following claims.

What is claimed is:

1. A carton having a plurality of adjustable air passages comprising:
   (a) a first tapered sleeve forming an outer carton unit, said first sleeve being closed at its bottom end and having a plurality of spaced openings therein; and
   (b) a second tapered sleeve forming an inner carton unit, said second sleeve being nested within said first sleeve and being slidable relative to said first sleeve along a vertical axis between a first position and a second position, said second sleeve being closed at its top end opposite said bottom closed end of said first sleeve and having a plurality of spaced openings therein arranged complimentarily to said spaced openings in said outer carton unit to align with the openings therein when said inner carton unit is in said first position, and to align with the spaces between said openings in said outer carton unit when said inner carton unit is in said second position, said first and second sleeves having rectangular cross-sections perpendicular to said vertical axis, and with the bottom end of the carton being larger than the upper end thereof, said closed top end of said second sleeve being formed by an opposite pair of flaps, each secured to the top of two opposed side walls by curved fold lines such that said closed end of said second sleeve is slightly bowed outwardly for improving the inherent frictional engagement between said relatively slidable first and second sleeve members thereby maintaining the positioning of said relatively slidable sleeve members at the desired degree of opening of said complimentary openings.

2. A carton as defined in claim 1 wherein the first and second sleeves are of substantially the same shape and dimension.

3. A carton as defined in claim 1 wherein both the first and second sleeves are constructed of paperboard.

4. A carton as defined in claim 1 wherein the openings in the first and second sleeves are of substantially the same size and dimension.

5. A carton as defined in claim 1 wherein the openings in the first and second sleeves are spaced vertically by a distance at least equal to the vertical dimension of the openings along a line parallel to the vertical axis.

6. A carton as defined in claim 1 wherein two opposed walls at said open top end of said first sleeve are partially cut away to permit grasping of said second sleeve to slide it within said first sleeve.

7. A carton as defined in claim 1 wherein the first and second sleeves both have substantially rectangular front and back panels and trapezoidal side panels.

* * * * *